United States Patent [19]

Gurmarnik

[11] Patent Number: 5,328,479
[45] Date of Patent: * Jul. 12, 1994

[54] SET FOR CONTINUOUS EPIDURAL ANESTHESIA

[76] Inventor: Simon Gurmarnik, 38 Garrison Rd., #1, Brooklyne, Mass. 02146

[*] Notice: The portion of the term of this patent subsequent to Aug. 16, 2005 has been disclaimed.

[21] Appl. No.: 64,213

[22] Filed: May 21, 1993

Related U.S. Application Data

[62] Division of Ser. No. 985,853, Dec. 4, 1992, Pat. No. 5,257,972.

[51] Int. Cl.5 ............................................. A61M 5/178
[52] U.S. Cl. .................................... 604/158; 604/117; 604/280; 604/51
[58] Field of Search ............... 604/116, 117, 164, 158, 604/173, 264, 280, 49, 51, 27, 28, 48; 128/898, 772

[56] References Cited

U.S. PATENT DOCUMENTS

| | | | |
|---|---|---|---|
| 4,760,847 | 8/1988 | Vaillancourt | 604/117 |
| 4,863,423 | 9/1989 | Wallace | 604/280 |
| 5,106,376 | 4/1992 | Mononen et al. | 604/48 |

Primary Examiner—C. Fred Rosenbaum
Assistant Examiner—Ronald K. Stright, Jr.
Attorney, Agent, or Firm—Ilya Zborovsky

[57] ABSTRACT

A set for continuous epidural anesthesia has an epidural catheter and a device for determining its required length and including an epidural needle insertable into an epidural space and a ruler with shorter and longer scales designed so that when the epidural needle is inserted in the epidural space and the ruler is placed against a skin and parallel to the needle while the epidural catheter is placed parallel to the ruller, the required length of the epidural catheter for anesthesia can be determined on the longer scale.

1 Claim, 1 Drawing Sheet

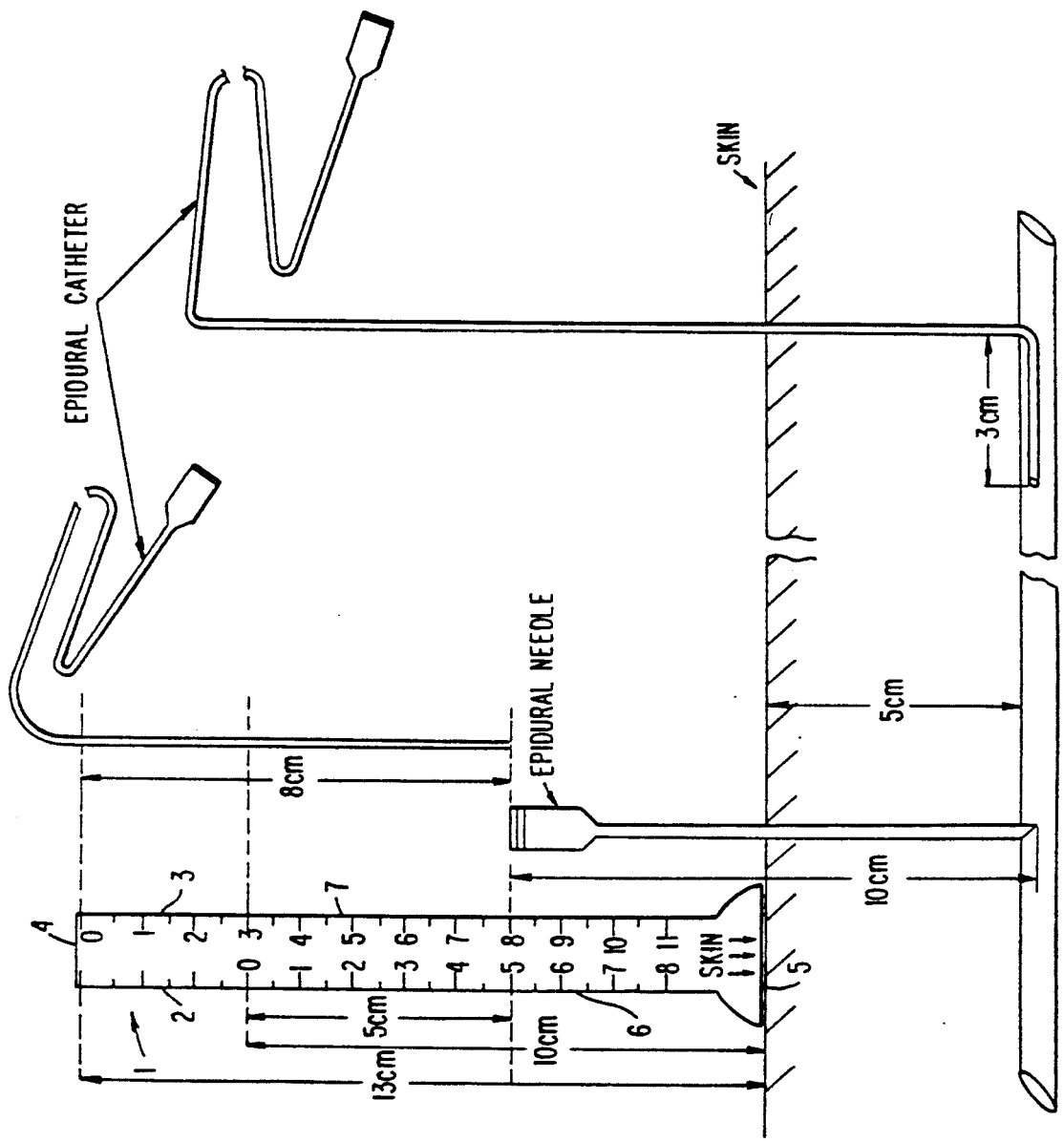

SET FOR CONTINUOUS EPIDURAL ANESTHESIA

CROSS REFERENCE TO A RELATED APPLICATION

This application is a division of application Ser. No. 07/985,853, filed Dec. 4, 1992, now U.S. Pat. No. 5,257,972.

BACKGROUND OF THE INVENTION

The present invention relates to a set for continuous epidural anesthesia which includes an epidural catheter and an epidural needle.

It is known that a standard procedure for the continuous epidural anesthesia requires localization of the epidural space by the epidural needle, then insertion of the epidural catheter through the epidural needle, then removal of the epidural needle and positioning of the catheter within the epidural space. Proper positioning of the epidural space is 2.5-3 cm inside the epidural space, and this proper position will minimize occurence of complications. Since the distance between the skin and the epidural space varies from 3 to 8 cm, every case requires a time consuming calculation of the length of the catheter with the graduated epidural needle and catheter.

It is known that in this procedure for a continuous epidural anesthesia .when the epidural catheter is utilized, the Catheter in the epidural space can be the cause of various iatrogenic complications. In order to avoid leaving too great a length in the lumbar epidural space during epidural anesthesia, graduated Tuochy needles can be used together with graduated epidural catheters. On the latter, a special marking shows that, when it reaches the needle hub, the catheter tip is at the needle bevel. Approximately 5-7 cm of the catheter length are introduced into the epidural space. The needle is removed and placed upside down next to the catheter with the hub in contact with the patient's skin. In this position the distance between the special marking on the catheter and the graduation on the needle which marks the skin level is equivalent to the length of the catheter in the epidural space. This distance and therefore the catheter length can then be reduced to about 4 cm by carefully withdrawing the catheter. Knowing exactly how much of the catheter is within the epidural space can be of particular importance whenever that space is uncommonly far from the patient's skin, due to obesity, oedema, use of paramedian route or a very oblique angle of the needle in the sagittal plane. The above described method is quite complicated and it is to be understood that it is desirable to improve the same.

In the stressful atmosphere of the operating room the above specified measurements and calculations present unnecessary hardships and usually are done with a great degree of inaccuracy.

SUMMARY OF THE INVENTION

Accordingly, it is an object of the present invention to provide a set which allows easy of determination of a required length of the epidural catheter for continuous epidural anesthesia, which avoids the disadvantages of the prior art.

In keeping with these objects and with others which will become apparent hereinafter, one feature of the present invention resides, briefly stated, in a set for epidural anesthesia which has an epidural catheter and means for its required length determination with an epidural needle and a ruler having two scales of different lengths, wherein one scale corresponds to a length of the epidural needle, while the other scale is longer than the one scale by a length corresponding to a required length of the epidural catheter inside the epidural space.

When the device is designed in accordance with the present invention it is substantially simpler to determine the required length of the epidural catheter by positioning the device on the skin and then placing the epidural catheter so that it extends from the hub of the epidural needle and therefore its required length is determined on the second longer scale.

The device makes significantly simpler the determination of the required length of the epidural catheter.

In accordance with another feature of the present invention, the longer scale has a length of 13 mm, while the shorter scale of the ruler has the length of 10 mm.

The novel features of the present invention are set forth in particular in the appended claims. The invention itself, however, both as to its construction and its method of operation will be best understood from the following description of preferred embodiments which is accompanied by the following drawing.

BRIEF DESCRIPTION OF THE DRAWING

The single FIGURE of the drawings is a schematic view showing a set for continuous epidural anesthesia, including an epidural catheter, and a device for determining its required length and including an epidural needle and a special ruler in accordance with the present invention.

DESCRIPTION OF THE PREFERRED EMBODIMENTS

A set for continuous epidural anesthesia includes an epidural catheter 111 and a device for determining its required length and including an epidural needle 11 and a ruler 1. The ruler is formed as an elongated member having two opposite sides 2 and 3, a top 4 and a bottom 5. One side 2 of the ruler is provided with a shorter scale 6 while the other side 3 of the ruler is provided with a longer scale 7.

The bottom 5 of the ruler 1 is used for placement of the ruler against a skin. The shorter scale is substantially equal to the total length of the epidural needle. It is used for instant determination of the distance between the skin and the epidural space, or in other words the distance from zero on the shorter scale 6 to the hub of the epidural needle 11.

The longer scale 7 is longer than the epidural needle and is used for the instant determination of the required length of-the epidural catheter 111. The longer scale is longer than the shorter scale by the required length of the epidural catheter inside the epidural space. The longer scale determines the required length of the epidural catheter which is equal to the distance from zero on the longer scale 7 to the hub of the epidural needle 11.

In the shown embodiment the shorter scale 6 is equal to 10 cm, while the longer scale 7 is equal to 13 cm, since the required length of the epidural catheter inside the epidural space is selected to be 3 cm.

The procedure of continuous epidural anesthesia with the device in accordance with the present invention is the same. In other words first the epidural space is localized by the epidural needle, then the epidural catheter is inserted through the epidural needle, then the epidural needle is removed, and the catheter is positioned within the epidural space. The determination of the required length of the catheter is performed in the following manner. When the epidural needle is inserted into the epidural space as shown in FIG. 1, the ruler is placed against the skin parallel to the epidural needle. Then the epidural catheter is positioned so that it extends from the hub of the epidural needle along the longer scale, and the required length of the epidural catheter can be immediately determined on the longer scale as shown in the drawings. In the shown example it has to be equal to 8 cm.

It will be understood that each of the elements described above, or two or more together, may also find a useful application in other types of constructions and methods differing from the types described above.

While the invention has been illustrated and described as embodied in a device and a method for length determination of the epidural catheter for the continuous epidural anesthesia, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A set for a continuous epidural anesthesia, comprising
   an epidural catheter for performing epidural anesthesia: and
   a device for determining a required length of said epidural catheter for administering epidural anesthesia and including an epidural needle insertable prior to administration of anesthesia into an epidural space and an element for determining the required length of said epidural catheter, said element being formed as a ruler and having two opposite sides, a shorter scale provided on one of said sides and having a length substantially corresponding to a length of said epidural needle, and a longer scale provided on the other of said sides and being longer than said shorter scale by a length corresponding to a required length of said epidural catheter inside said epidural space, so that when said epidural needle is inserted in the epidural space and said ruler is placed against a skin parallel to said epidural needle, then when said epidural catheter is placed parallel to said ruler extending from a hub of said epidural needle along said longer scale, its length between the hub of said epidural needle and a beginning of said longer scale corresponds to a required length of said epidural catheter to be inserted into a patient said shorter scale having a length of substantially 10 cm, while said longer scale has a length of substantially 13 cm.

* * * * *